United States Patent [19]

Miller

[11] Patent Number: 4,824,954

[45] Date of Patent: Apr. 25, 1989

[54] PROCESS FOR PREPARATION OF SUBSTITUTED PYRIDINES

[75] Inventor: Maria L. Miller, Manchester, Mo.

[73] Assignee: Monsanto Company, St. Louis, Mo.

[21] Appl. No.: 768,658

[22] Filed: Aug. 27, 1985

Related U.S. Application Data

[63] Continuation-in-part of Ser. No. 668,850, Nov. 6, 1984, abandoned.

[51] Int. Cl.⁴ ............................................. C07D 211/02
[52] U.S. Cl. .................................... 546/250; 546/310
[58] Field of Search ........................ 546/250, 251, 310

[56] References Cited

PUBLICATIONS

Rappoport, Z. "The Chemistry of the Cyano Group" Interscience Publishers (1970) pp. 378–383.
House, H. O. "Modern Synthetic Methods" Benjamin Cummings Publishing Co. (1972) pp. 546–549, 570–573, 766–769.
Klingsberg, E. Pyridine and its Derivatives Pt. 1 (1960) p. 309.

Primary Examiner—Jane T. Fan
Attorney, Agent, or Firm—James C. Bolding

[57] ABSTRACT

Disclosed herein is a novel process for the preparation of 4-amino-3,5-pyridinedicarboxylate derivatives by (a) reaction of an acetonediester with a primary amine to form an enamine, (b) reaction with a carboxylic acid anhydride or halide to form a 2-alkylcarbonyl-3-amino-2-pentenedicarboxylate, and (c) reaction with a halogenated alkylnitrile to form the pyridinedicarboxylate product. The product is useful as a herbicide or an intermediate in the formation of a herbicide.

8 Claims, No Drawings

PROCESS FOR PREPARATION OF SUBSTITUTED PYRIDINES

This is a continuation-in-part of application Ser. No. 668,850, filed Nov. 6, 1984 now abandoned.

This invention relates to the preparation of 4-amino pyridinedicarboxylic acids and esters having fluoroalkyl substitution at the 2 and 6 positions.

Pyridine derivatives and derivatives of nicotinic acid have been investigated for many years for use in the biological sciences. Such compounds have been prepared by a variety of methods.

In U.S. Pat. No. 3,748,334 there is disclosed a method of preparation of a 4-hydroxy-2,6-bis(trifluoromethyl)-pyridine by cyclization of a heptanetrione of the formula

with aqueous ammonia to obtain the ammonium salt of the pyridinol, followed by neutralization of the pyridinol.

A method of obtaining a 2- or 6- fluoroalkyl-3-pyridinemonocarboxylate compound is disclosed in U.S. Pat. No. 3,534,056. This method involves the reaction of nicotinic acid N-oxide with hexafluoropropene. The product obtained is a mixture of the 2 and 6-substituted tetrafluoroethyl nicotinic acid.

BRIEF DESCRIPTION OF THE INVENTION

An object of this invention is to provide novel methods for preparing the novel pyridine compounds useful as herbicides.

The novel compounds prepared by the process of this invention are useful as herbicides or intermediates in the preparation of herbicides and are represented by the generic formula

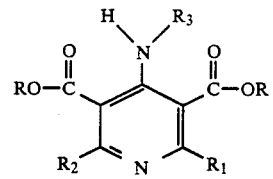

wherein:
R is lower alkyl;
$R_1$ and $R_2$ are independently selected from fluorinated and chlorofluorinated lower alkyl radicals; and
$R_3$ is independently selected from lower alkyl, aralkyl, and cycloalkyl.

The term "alkyl" means both straight and branched chain radicals which include, but are not limited to, ethyl, methyl, n-propyl, 1-ethylpropyl, 1-methylpropyl, n-butyl, 2,2-dimethylpropyl, pentyl, hexyl, heptyl, isobutyl, isopropyl. The term "cycloalkyl" means saturated cyclic radicals such as cyclopropyl, cyclobutyl, cyclopentyl, cyclohexyl, and cycloheptyl.

The term "lower alkyl" herein means an alkyl radical having 1 to 7 carbon atoms.

The term "fluorinated alkyl" means alkyl radicals having one or more fluorine atoms attached thereto including radicals wherein all hydrogen atoms replaced by fluorine.

The term "chlorofluorinated alkyl" means an alkyl radical having at least one hydrogen replaced by fluorine and at least one other hydrogen replaced by chlorine.

The term "aralkyl" means alkyl-substituted aryl radicals such as benzyl and the like.

The process of preparation of pyridine dicarboxylate compounds of the present invention is shown schematically in the route below.

PROCESS OF THE INVENTION

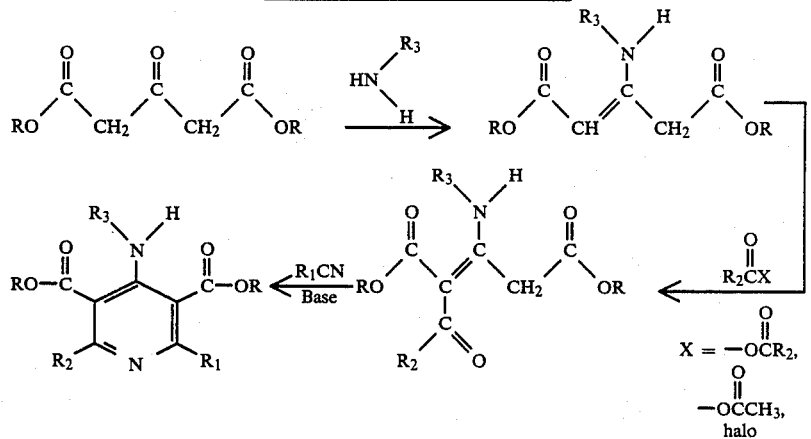

In the process, a pentane-3-one-dioate ester, also referred to as an acetonedicarboxylate, is reacted with an appropriate primary amine in a suitable reaction medium to provide a 3-amino-2-pentenedicarboxylate (enamine diester). The reaction medium employed in this step is not narrowly critical; the acetonedicarboxylate may be employed alone or a solvent such as an ether may be used. The reaction proceeds smoothly at low temperatures (0°–50° C.) although temperatures up to reflux may be used. The reaction is exothermic.

The reaction proceeds in the liquid phase and need not be performed at elevated temperatures and pressures, although pressures above atmospheric may be employed if desired.

In the second step of the process, the enamine diester is reacted with fluorinated or chlorofluorinated alkyl acid halide, anhydride or mixed anhydride in which the fluorinated or chlorofluorinated alkyl moiety of the acid anhydride becomes the radical $R_2$ in the ultimate pyridinedicarboxylate compound. In this reaction step, a solvent may optionally be employed; suitable solvent media include diethyl ether, and tetrahydrofuran, with or without a tertiary amine such as triethylamine. Temperatures in the range of about 0° C. to ambient are sufficient for this reaction, although lower or higher temperatures may be used.

The third step of the process involves the reaction of the 2-alkylcarbonyl-3-amino-2-pentenedicarboxylate produced in step 2 with a fluorinated or chlorofluorinated acetonitrile to form a 4-amino pyridine dicarboxylate compound. Again, as in step 2 of the process, dimethyl or diethyl ethers, toluene, or the like are suitable solvent media and an amine base such as triethylamine, potassium t-butoxide or DBU is employed. Temperatures of −60° C. to 50° C. are generally sufficient for this reaction step. When higher temperatures are to be used, superatmospheric pressures may be required because of the volatility of the halogenated acetonitrile.

A better appreciation of the present invention will be gained by reference to the following Examples.

As used throughout the specification, including the Examples, the following abbreviations have the following meanings:

THF—tetrahydrofuran
DME—dimethoxyethane
DMF—N,N-dimethylformamide
HPLC—high pressure liquid chromatography
TLC—thin layer chromatography
DMSO—dimethyl sulfoxide
DBU—1,8-diazobicyclo-[5.4.0]-undec-7-ene

PREPARATION OF PYRIDINE DICARBOXYLATES VIA THE PROCESS OF THE INVENTION

The following Examples illustrate the preparation of pyridine compounds using the enamine diester method of this invention. Examples 1, 2, 4, 7, 9, and 11 illustrate the preparation of the enamine diester compounds themselves from the acetonedicarboxylate starting material and Examples 1, 2, 4–9, 11, and 12 illustrate the reaction of the enamine diester with a fluorinated or chlorofluorinated alkyl anhydride. Examples 1–12 show the preparation of 4-amino pyridinedicaroxylate compounds by reaction of the resulting 3-amino-2-fluoroalkyl or chlorofluoroalkyl-2-pentenedioate intermediate with a fluorinated or chlorofluorinated acetonitrile.

EXAMPLE 1

Diethyl 4-cyclopropylamino-2,6-bis(chlorodifluoromethyl)-3,5-pyridinedicarboxylate Step A: Preparation of diethyl 3-cyclopropylamino-2-pentenedioate: To 30.33 g (0.15 mol) of diethyl acetonedicarboxylate was added dropwise 11.8 g (0.19 mol) of cyclopropylamine at such a rate that reaction temperature was kept below 48° C. The reaction mixture was stirred at room temperature for 18 hours. The reaction mixture was poured into H$_2$O, extracted twice with ether, dried (MgSO$_4$) and concentrated in vacuo affording 34.42 g of a light yellow oil. The crude was kugelrohr distilled at 53 Pa and collected at a pot temperature of 102–104° C. to give 23.73 g (66%) of enamine diester as a light yellow oil, $n_D^{25}$ 1.5025.

Anal. Calc'd. for $C_{12}H_{19}N_1O_4$: C, 59.73; H, 7.94; Found: C, 59.57; H, 7.96.

Steps B and C: Preparation of pyridinedicarboxylate product: To an ice-cooled solution of 24.1 g (0.1 mol) of the enamine diester from Step A, and 12.14 g (17 ml, 0.12 mol) of triethylamine in 75 ml of anhydrous ether was added dropwise 34.16 g (0.14 mol) of chlorodifluoroacetic anhydride at such a rate that the reaction temperature was kept below 10° C. After stirring at room temperature for 2 hours, the reaction mixture was poured into water, extracted with ether, dried (MgSO$_4$) and concentrated to give 35 g (99% yield, 74% pure) of a brown oil. A portion of this crude material was then reacted as follows:

To 65 ml of DME cooled to 5° C. in a magnetically stirred flask with thermometer and dry-ice condenser was added 14.5 g (0.13 mol) of CF$_2$ClCN via subsurface tube. To this solution 21.21 g (0.06 mol) of the crude product of Step B was added, followed by 16.7 ml (0.12 mol) of triethylamine. The reaction mixture was warmed to 25° C., resulting in mild reflux of the nitrile. Dry ice was maintained in the condenser for 2 hours and the reaction mixture is stirred at 25° C. for 18 hours. The reaction mixture was poured into 2% HCl/3% NaCl solution, and extracted twice with CH$_2$Cl$_2$. The combined extracts were washed with 1% HCl/3% NaCl, then twice with 1% NaOH/3% NaCl solution. After drying (MgSO$_4$), the extracts were filtered, concentrated, and the residue (18.92 g of a dark brown oil) kugelrohr distilled at 110°–160° C./67 Pa affording 12.94 g (56%) of a thick amber oil. For elemental analysis a 2 g portion was purified by HPLC using 10% ethyl acetate/cyclohexane as eluting solvent, followed by kugelrohr distillation at 130°–160° C./106 Pa affording 1.66 g of product as a yellow oil, $n_D^{25}$ 1.5350.

Anal. Calc'd. for $C_{16}H_{16}F_4Cl_2N_2O_4$: C, 42.97; H, 3.61; N, 6.26; Cl, 15.85; Found: C, 43.03; H, 3.65; N, 6.24; Cl, 15.79.

EXAMPLE 2

Diethyl 2,6-bis(trifluoromethyl)-4-benzylamino-3,5-pyridinedicarboxylate

Step A: Preparation of diethyl 3-benzyl-amino-2-pentenedioate: Into a 1 L 3-necked RB-flask equipped with mechanical stirrer and thermometer was placed 182 ml (202 g, 1.0 mol) of diethylacetone dicarboxylate and added dropwise 131 ml (128.6 g, 1.2 mol) of benzylamine in such rate that reaction temperature was kept below 45° C. The mixture was stirred at room temperature for 3 hours (G.C. of crude showed no more starting material). The reaction mixture was poured into H$_2$O and extracted twice with Et$_2$O. Combined Et$_2$O layers were washed with saturated aqueous NaCl. The Et$_2$O layer was dried (MgSO$_4$) and solvent removed in vacuo affording 285 g of a yellow oil. Crude was kugelrohr at 60 Pa and collected at a pot temperature of 130°–160° C. to give 252.71 g (87%) of product as a white solid; mp 34°–36° C.

Anal. Calc'd. for $C_{16}H_{21}N_1O_4$: C, 65.96; H, 7.27; N, 4.81; Found: C, 65.91; H, 7.32; N, 4.79.

Step B: Preparation of diethyl 3-benzylamino-2-trifluoroacetyl-2-pentenedioate hemihydrate: To a 3 L 4-necked RB-flask equipped with mechanic stirrer, internal thermomemter, dropping funnel and nitrogen gas inlet was placed 252.7 g (0.87 mol) of product of Step A and 132 ml (96.1 g, 0.95 mol) of triethylamine in 1 L of anhydrous $Et_2O$. This solution was cooled to 0° C. and 129 ml (191.7 g, 1.0 mol) of trifluoroacetic anhydride was added dropwise at such a rate that reaction temperature remained below 10° C. The reaction mixture was stirred at 0° C. for one-half hour and then warmed to room temperature slowly. This reaction was followed by TLC (10% EtOAc/cyclohexane) and usually was completed in 3 to 10 hours. When no more starting material was observed by TLC the mixture was poured into $H_2O$ and extracted twice with $Et_2O$. The $Et_2O$ layer was dried ($MgSO_4$) and solvent removed in vacuo affording a yellow solid. Crude solid was washed with hexane and dried in vacuo affording 240.84 g (72%) of product as a yellow solid; mp 63°–65° C.

Anal. Calc'd. for $C_{18}H_{20}F_3N_1O_5[0.5\ H_2O]$: C, 54.54; H, 5.34; N, 3.53; Found: C, 54.67; H, 5.11; N, 3.41.

Step C: Preparation of pyridinedicarboxylate product: To a 0° C. solution of 16.02 g (0.169 mol) of $CF_3CN$ in 60 ml of DME in a flask equipped with dry-ice condenser was added dropwise a solution of 30 g (0.080 mol) of product of Step B in 25 ml of DME. The reaction temperature was allowed to rise to 5° C. and 16.1 g ;22.17 ml, 0.160 mol) of triethylamine was added at such a rate that the reaction temperature did not rise above 10° C. Reaction mixture was allowed to come to room temperature and stirred for 2 hours, then poured into 2% HCl and extracted with diethyl ether. The ether phase was washed with 2% NaOH, and dried ($MgSO_4$). The dry ether phase was concentrated in vacuo yielding 28.0 g of a gold crystalline material. This was kugelrohr distilled at 67 Pa and collected at a pot temperature of 154°–155° C. affording 16.0 g (44%) of a yellow-gold crystalline solid product; mp 58°–62° C.

Anal. Calc'd. for $C_{20}H_{18}F_6N_2O_4$: C, 51.73; H, 3.91; N, 6.03; Found: C, 51.74; H, 3.95; N, 6.00.

EXAMPLE 3

Diethyl 6-(chlorodifluoromethyl)-4-benzylamino-2-trifluoromethyl)-3,5-pyridinedicarboxylate Into a 3 L 4-necked RB-flask equipped with mechanical stirrer, internal thermometer, dry ice acetone condenser and $N_2$inlet was placed 650 ml of DME at 0° C. To this was added 145 g (1.30 mol) of $CF_2ClCN$ followed by 240.84 g (0.62 mol) of crude product of Step B of Example 2 in 700 ml of DME. To this solution at 0° C. was added 181 ml (131.5 g, 1.30 mol) of triethylamine at such a rate that the reaction temperature was kept below 10° C. This mixture was stirred at 0° C. for one-half hour and then warmed up slowly to 25° C. After stirring at 25° C. for 3 hours, TLC (10% EtOAc/cyclohexane) and G.C. showed that the reaction was complete. This mixture was poured into 4% HCl/2% NaCl and extracted twice with ether. The combined $Et_2O$ layers were washed twice with 5% NaOH/2% NaCl. The $Et_2O$ layer was dried ($MgSO_4$) and solvent removed in vacuo affording 260.89 g of a yellow solid. Crude was recrystallized from hot hexane affording 234.74 g (79%) of product as a yellow solid; mp 49°–53° C.

Anal. Calc'd. for $C_{20}H_{18}Cl_1F_5N_2O_4$: C, 49.96; H, 3.77; N, 5.83; Cl, 7.37; Found: C, 50.02; H, 3.78; N, 5.76; Cl, 7.38.

EXAMPLE 4

Dimethyl 2-(chlorodifluoromethyl)-4-(cyclopropylamino)-6-(difluoromethyl)-3,5-pyridinedicarboxylate Step A: Preparation of dimethyl 3-(cyclopropylamino)-2-pentenedioate.

To a solution of 190.6 g (1.09 mol) of dimethyl acetonedicarboxylate in 200 ml of ether was added 75 g (1.3 mol) of cyclopropylamine dropwise. After stirring for 4 hours at 25° C. the solution was diluted with 200 ml of ether, washed with two 300 ml portions of 2% aqueous NaCl solution, dried ($CaSO_4$), filtered and concentrated to 194 g of clear oil. Trituration with petroleum ether gave 171.5 g (74%) of the enamine diester as a white solid: mp 64°–70° C. Crystallization from cyclohexane afforded an analytical sample; mp 73°–75° C.

Anal. Calc'd. for $C_{10}H_{15}N_1O_4$: C, 56.33; H, 7.09; N, 6.57; Found: C, 56.49; H, 7.12; N, 6.54.

Step B: Preparation of dimethyl 3-(cyclopropylamino)-2-difluoroacetyl-2-pentenedioate.

A solution of 25 g (0.26 mol) of difluoroacetic acid in 200 ml of ether was allowed to react with 6.25 g (0.26 mol) of sodium hydride. After hydrogen evolution ceased, 20.4 g (0.26 mol) of acetyl chloride was added dropwise. The solution was allowed to stir overnight at 25° C. The crude was filtered through celite and concentrated to a yellow oil. Distillation (130°–135° C., 101 kPa) gave 19 g of clear liquid which was a 4:3:3 mixture of α,α-difluoroacetic anhydride:acetic acid: difluoroacetic acid. A slurry of 10 g (0.047 mol) of product from Step A in 100 ml of ether at 5° C. was allowed to react with 17.6 g of the anhydride mixture prepared above, which contained 0.051 mol of the anhydride. Soon after addition the solution became homogeneous. After 2 hours at 25° C. the reaction was complete. The crude mixture was diluted with 100 ml of ether, washed with three 300 ml portions of 5% aqueous sodium bicarbonate, dried ($CaSO_4$), filtered and concentrated to 10.6 g (78%) of a yellow oil, $n_D^{25}$ 1.5127.

Anal. Calc'd. for $C_{12}H_{15}F_2N_1O_5$: C, 49.49; H, 5.19; N, 4.81; Found: C, 49.10; H, 5.22; N, 4.78.

Step C: Preparation of Pyridinedicarboxylate Product.

Into a flask containing 200 ml of DME at −10° C. was bubbled 5 g (0.045 mol) of chlorodifluoroacetonitrile. To this was added 5 g (0.017 mol) of product of Step B in 100 ml of DME followed by 5.6 g (0.037 mol) of DBU. This was allowed to warm slowly to room temperature.

After reaching 25° C. the solution was poured into 500 ml of 4% HCl/2% NaCl and extracted with ether. The ether layer was washed with two 500 ml portions of 5% NaOH/2% NaCl, dried ($CaSO_4$), filtered and concentrated to 3.9 g of red oil. This oil was dissolved in ether and filtered through silica gel. Evaporation of the ether gave 1.7 g (26%) of product as an off-white solid; mp 70°–74° C.

Anal. Calc'd. for $C_{14}H_{13}Cl_1F_4N_2O_4$: C, 43.71; H, 3.41; N, 7.28; Found: C, 43.45; H, 3.44; N, 7.18.

EXAMPLE 5

Dimethyl 2,6-bis(chlorodifluoromethyl)-4-(cyclopropylamino)-3,5-pyridinedicarboxylate Step B: Preparation of dimethyl 3-(cyclopropylamino)-2-chlorodifluoroacetyl-2-pentenedioate:

To a slurry of 30 g (.14 mol) of product of Step A of Example 4 in 300 ml of ether at 0° C. was added 38.9 g (0.16 mol) of chlorodifluoroacetic anhydride dropwise. After addition was complete the mixture was allowed to warm slowly to room temperature. After 1 hour at 25° C. the homogeneous solution was washed with three 300 ml portions of 5% aqueous sodium bicarbonate, dried (CaSO$_4$), filtered and concentrated to a semi-solid. Recrystallization from ether-petroleum ether gave the product as a white solid; mp 55°–57° C.

Anal. Calc'd. for $C_{12}H_{14}Cl_1F_2N_1O_5$: C, 44.25; H, 4.33; N, 4.30; Found: C, 44.00; H, 4.23; N, 4.25.

Step C: Preparation of Pyridinedicarboxylate Product

To a flask containing 250 ml of DME at −60° C. was bubbled in 4.4 g (0.4 mol) of chlorodifluoroacetonitrile. To this solution was added 6 g (0.018 mol) of product of Step A in 100 ml of 1,2-dimethoxyethane. This was followed by addition of 2.74 g (0.018 mol) of DBU. This solution was then allowed to warm slowly to 25° C. and remain at that temperature for 18 hours. The crude was poured into 500 ml of 4% HCl/2% NaCl, and extracted with ether. The ether layer was washed with two 500 ml portions of 5% NaOH/2% NaCl, dried (CaSO$_4$), filtered and concentrated to give 7.7 g of orange oil. Crystallization from ether-petroleum ether gave 6.3 g (84%) of product as a white solid: mp 90°–92.5° C.

Anal. Calc'd. for $C_{14}H_{12}Cl_2F_4N_2O_4$C, 40.12; H, 2.89; N, 6.68; Found: C, 40.26; H, 2.97; N, 6.69.

EXAMPLE 6

Diethyl 2-chlorodifluoromethyl-4-cyclopropylamino-6-trifluoromethyl-3,5-pyridinedicarboxylate Step B: Preparation of diethyl 3-cyclopropylamino-2-trifluoroacetyl-2-pentenedioate:

To a 0° C. solution of 6.03 g (0.025 mol) of product of Step A of Example 1 and 2.53 g (3.7 ml, 0.025 mol) of triethylamine in 50 ml of anhydrous Et$_2$O was added dropwise 5.25 g (3.5 ml, 0.025 mol) of trifluoroacetic anhydride at such a rate that reaction temperature was kept below 10° C. The reaction mixture was stirred at 0° C. for one-half hour and then poured into 10% HCl, extracted twice with Et$_2$O and dried (MgSO$_4$). Solvent was removed in vacuo, and the crude mixture was purified by HPLC using 10% EtOAc/cyclohexane to afford 6.45 g of a yellow oil. This oil was kugelrohr distilled at 115°–120° C./53 Pa to give 5.53 g (66%) of product as a light yellow oil, n$_D^{25}$ 1.4792.

Anal. Calc'd. for $C_{14}H_{18}F_3N_1O_5$: C, 49.85; H, 5.38; N, 4.15; Found: C, 50.04; H, 5.37; N, 3.94.

Step C: Preparation of pyridinedicarboxylate product:

To 20 g of DME cooled to 5° C. in a magnetically stirred flask with thermometer and dry ice condenser is added 3.5 g (0.031 mol) of CF$_2$ClCN via subsuface tube. To this solution 5.0 g (0.015 mol) of crude product of Step A is added followed by 3.0 g (0.030 mol) of triethylamine. The reaction mixture is warmed to 25° C., resulting in mild reflux of the nitrile. Dry ice was maintained in the condenser for 2 hours and the reaction mixture was stirred at 25° C. for 18 hours. The reaction mixture was poured into 150 ml of 1% HCl/3% NaCl, extracted with CH$_2$Cl$_2$(1×150 ml, 2×25 ml). The combined extracts were washed with 150 ml of 1% HCl/3% NaCl, then twice with 100 ml of 1% NaOH/3% NaCl solution. After drying (MgSO$_4$), the extracts were filtered, concentrated and the residue kugelrohr distilled at 150°–170° C./20 Pa to give 3.61 g (56% yield from product of Step A) of product as a yellow oil, n$_D^{25}$ 1.4869.

Anal. Calc'd. for $C_{16}H_{16}Cl_1F_5N_2O_4$: C, 44.61; H, 3.74; N, 6.50; Found: C, 44.89; H, 3.88; N, 6.25.

EXAMPLE 7

Diethyl 2-(chlorodifluoromethyl)-4-(cyclobutylamino)-6-(trifluoromethyl)-3,5-pyridinedicarboxylate Step A: Preparation of diethyl 3-cyclobutylamino-2-pentenedioate:

Into a 100 ml 3-necked round bottomed flask equipped with magnetic stirrer, dropping funnel and thermometer was placed 20.22 g (18.2 ml, 0.1 mol) of diethylacetonedicarboxylate and then was added dropwise 7.8 g (9.8 ml, 0.11 mol) of cyclobutylamine at such a rate that reaction temperature was kept below 45° C. The reaction mixture turned light yellow and cloudy. The mixture was stirred at room temperature for one-half hour and then poured into 150 ml of H$_2$O. The product was extracted with Et$_2$O (2×150 ml), washed with 150 ml of saturated NaCl solution, dried (MgSO$_4$) and solvent removed in vacuo affording 23.57 g of a light yellow oil. The crude mixture was kugelrohr distilled at 0.6 torr (pot temperature 90°–105° C.) affording 22.53 g (88%) of product as a colorless oil, n$_D^{25}$ 1.5063.

Anal. Calc'd. for $C_{13}H_{21}N_1O_4$: C, 61.16; H, 8.29; N, 5.49; Found: C, 61.08; H, 8.31; N, 5.25.

Step B: Preparation of diethyl 3-(cyclobutylamino)-2-(trifluoroacetyl)-2-pentenedioate:

To a 250 ml 3-necked round bottomed flask equipped with magnetic stirrer, internal thermometer, dropping funnel and N$_2$gas inlet was placed 20.34 g (0.08 mol) of product of Step A in 75 ml of anhydrous Et$_2$O. This solution was cooled to 0° C. and 18.21 g (12 ml, 0.095 mol) of trifluoroacetic anhydride was added dropwise at such a rate that the reaction temperature was kept below 10° C. Then the reaction mixture was warmed to 20° C., poured into 150 ml of H$_2$O and extracted with Et$_2$O (2×150 ml). Combined Et$_2$O layers were washed with 100 ml of 2% aqueous NaHCO$_3$and 100 ml of saturated NaCl, and dried (MgSO$_4$). Solvent was removed in vacuo affording 28 g (99%) of crude material as a light yellow oil and which by G.C. showed to be 97% pure. A portion of this oil was purified using the HPLC and 5% EtOAc/cyclohexane as eluting solvent affording a product as a yellow solid; mp 31°–32° C.

Anal Calc'd. for $C_{15}H_{20}F_3N_1O_5$: C, 51.28; H, 5.74; N, 3.99; Found: C. 51.38; H, 5.75; N, 3.72.

Step C: Preparation of pyridinedicarboxylate product:

Into a 500 ml 3-necked round bottomed flask equipped with magnetic stirrer, internal thermometer, dry-ice condenser, dropping funnel and nitrogen gas inlet was placed a solution of 22.4 g (0.06 mol) of product of Step B in 250 ml of DME. This solution was cooled to −40° C. and 14.2 g (0.12 mol) of CF$_2$ClCN were added, followed by addition of 9.13 g (9 ml, 0.06 mol) of DBU. Then the reaction mixture was warmed to room temperature and left stirred overnight. G.C. analysis of crude reaction mixture showed some starting material and additional CF$_2$ClCN was added at room temperature (using a dry-ice acetone condenser) until no more starting material was observed by G.C. This mixture was poured into 4% HCl/2% NaCl (500 ml) and extracted twice with Et$_2$O (2×500 ml). Combined Et$_2$O layers were washed twice (2×300 ml) with 5% NaOH/2% NaCl, dried (MgSO$_4$) and solvent removed in vacuo. The remaining DME was removed by kugelrohr distillation at 0.5 torr (pot temperature 50° C.) affording 22.62 g (85%) of product as a brown oil with a purity higher than 90% by G.C. A portion of this thick brown oil was purified using HPLC and 5% EtOAc/cyclohexane as eluting solvent followed by kugelrohr distillation at 0.4 torr (pot temperature 100°–120° C.) to give product as a light yellow oil, n$_D^{25}$ 1.4873.

Anal. Calc'd. for C$_{17}$H$_{18}$Cl$_1$F$_3$N$_2$O$_4$: C, 45.91; H, 4.08; N, 6.30; Cl, 7.97%; Found: C, 46.13; H, 4.08: N, 6.27; Cl, 8.06.

EXAMPLE 8

Dimethyl 4-(cyclopropylamino)-2,6-bis(trifluoromethyl)-3,5-pyridinedicarboxylate Step B: Preparation of dimethyl 3-(cyclopropylamino)-2-(trifluoroacetyl)-2-pentenedioate:

To a 0° C. solution of 40 g (0.19 mol) of product of Step A of Example 4 in 300 ml of anhydrous Et$_2$O was added dropwise 39.9 g (27 ml, 0.19 mol) of trifluoroacetic anhydride at such a rate that the reaction temperature was kept below 10° C. Then the reaction was warmed to room temperature and poured into 500 ml of H$_2$O. The Et$_2$O layer was separated, washed twice with saturated NaHCO$_3$ (2×300 ml), washed again with saturated NaCl (300 ml) and then dried (MgSO$_4$). Solvent was removed in vacuo affording 52.59 g of a light yellow solid. This solid was recrystallized in Et$_2$O/hexane affording 49.46 g (84%) of a white solid; mp 51.5°–52.5° C.

Anal. Calc'd. for C$_{12}$H$_{14}$F$_3$N$_1$O$_5$: C, 46.73; H, 4.57; N, 4.52; Found: C, 46.73; H, 4.57; N, 4.52.

Step C: Preparation of pyridinedicarboxylate product:

To a 500 ml 4-necked round bottomed flask equipped with magnetic stirrer, thermometer and dry-ice condenser was placed 20 g (0.065 mol) of product of Step A in 250 ml of DME. The resulting solution was cooled to −30° C. and 12.35 g (0.13 mol) of CF$_3$CN were added followed by dropwise addition of 9.9 g (9.7 ml, 0.065 mol) of DBU. The resulting mixture was warmed slowly to room temperature and left to stir for 16 hours. An additional 1 g (1 ml, 0.006 mol) of DBU and 6 g (0.06 mol) of CF$_3$CN were added at room temperature using a dry-ice acetone condenser and stirred for 48 hours. The reaction mixture was then poured into 300 ml of 3% HCl, extracted twice with Et$_2$O (2×300 ml.). The combined Et$_2$O layers were washed with 300 ml of 3% HCl, washed twice with 2% NaOH (2×250 ml) and dried (MgSO$_4$). The solvent was removed in vacuo affording 14.2 g of a sticky yellow solid. The crude product was dissolved in CH$_3$OH/hexane and crystallized cold by adding Et$_2$O to give 10.81 g (43%) of a light beige solid. A portion of this solid was purified using HPLC and 10% EtOAc/cyclohexane as eluting solvent to give an analytical sample as a light beige solid; mp 71°–72° C.

Anal. Calc'd. for C$_{14}$H$_{12}$F$_6$N$_2$O$_4$: C, 43.53; H, 3.13; N, 7.25; Found: C, 43.51; H, 3.16; N, 7.24.

EXAMPLE 9

Dimethyl 4-benzylamino-2-(chlorodifluoromethyl)-6-(trifluoromethyl)-3,5-pyridinedicarboxylate Step A: Preparation of dimethyl 3-(benzylamino)-2-pentenedioate:

To a solution of 348 g (2 mol) of dimethylacetonedicarboxylate in 400 ml of anhydrous Et$_2$O was added slowly 214.32 g (218.5 ml, 2 mol) of benzylamine. During the addition Et$_2$O refluxed mildly and the reaction mixture was stirred at room temperature for 16 hours. Crude was poured into H$_2$O, and extracted twice with Et$_2$O. The combined Et$_2$O layers were washed with saturated NaCl and dried (MgSO$_4$). Solvent was removed in vacuo affording 524.46 g of a light yellow solid. This crude material was recrystallized in EtOAc/hexane affording 461.94 g (88%) of product as a beige solid; mp 67°–69° C.

Anal. Calc'd. for C$_{14}$H$_{17}$N$_1$O$_4$: C, 63.87; H, 6.51; N, 5.32; Found: C, 63.78; H, 6.51; N, 5.31.

Step B: Preparation of dimethyl 3-(benzylamino)-2-(trifluoroacetyl)-2-pentenedioate:

To a 3 L 3-necked round bottomed flask equipped with mechanical stirrer, dropping funnel and nitrogen inlet was placed 263 g (1 mol) of product of Step A in 2 L of anhydrous Et$_2$O. This mixture was cooled to 0° C. and 191.7 g (130 ml, 1 mol) of trifluoroacetic anhydride was added dropwise. This reaction mixture was warmed up to 20° C. and a white precipitate formed making stirring difficult. After stirring at room temperature for one-half hour the reaction mixture was poured into H$_2$O, extracted with EtOAc, and the EtOAc layer washed with saturated NaHCO$_3$. The EtOAc layer was dried (MgSO$_4$) and concentrated to 421.35 g of a yellow solid. The crude material was washed with hexane affording 320.12 g (89%) of product as a beige solid; mp 89.5°–90.5° C.

Anal. Calc'd. for C$_{16}$H$_{16}$F$_3$N$_1$O$_5$: C, 53.49; H, 4.49; N, 3.90; Found: C, 53.54; H, 4.49; N, 3.90.

Step C: Preparation of pyridinedicarboxylate product:

Into a 5 L 4-necked round bottomed flask equipped with mechanical stirrer, internal thermometer, dry-ice condenser, dropping funnel and nitrogen gas inlet was placed a solution of 317.27 g (0.88 mol) of product of Step B in 2.5 L of DME. This solution was cooled to −30° C. and 200 g (1.7 mol) of CF$_2$ClCN were added, followed by addition of 156.8 g (154 ml, 1.03 mol) of DBU. This reaction mixture was warmed to room temperature and left to stir overnight. Analysis (G.C.) of crude reaction mixture showed some starting material and additional CF$_2$ClCN was added at room temperature (using a dry-ice acetone condenser) until no more starting material was observed by G.C. This mixture was poured into 3.7% HCl, extracted twice with Et$_2$O, combined Et$_2$O layer washed with 5% NaOH/2% NaCl and dried (MgSO$_4$). Solvent was removed in vacuo to give 381.98 g (96%) of crude product as a yellowish brown solid: mp 56°–59° C. Crystallization from Et$_2$O/hexane afforded an analytical sample of product as a yellow solid; mp 68.0°–69.5° C.

Anal. Calc'd. for $C_{18}H_{14}Cl_1F_5N_2O_4$: C, 47.75; H, 3.12; N, 6.19; Found: C, 47.65; H, 3.15; N, 6.19.

EXAMPLE 10

Dimethyl 2-(dichlorofluoromethyl)-4-(cyclopropylamino)-6-(trifluoromethyl)-3,5-pyridinedicarboxylate To a solution of 5 g (0.016 mol) of product of Step A of Example 8 and 4.1 g (0.032 mol) of dichlorofluoroacetonitrile in 50 ml of DME at $-30°$ C. was added 2.5 g (0.016 mol) of DBU. After addition was complete the solution was allowed to warm slowly to room temperature. After 1 hour at 25° C. the solution was diluted with ether, washed with two 200 ml portions of 5% HCl, one 200 ml portion of 5% NaOH, and one 200 ml portion of water, dried (CaSO$_4$), filtered and concentrated to 4 g (60%) of product as a yellow oil, $n_D^{25}$ 1.5105.

Anal. Calc'd. for $C_{14}H_{12}Cl_2F_4N_2O_4$: C, 40.17; H, 2.89; N, 6.68; Found: C, 40.21; H, 2.93; N, 6.66.

EXAMPLE 11

Diethyl 6-chlorodifluoromethyl-4-(isopropylamino)-2-trifluoromethyl-3,5-pyridinedicarboxylate Step A: Preparation of diethyl 3-isopropylamino-2-pentenedioate:

Isopropylamine (60 ml, 0.712 mol) was added slowly to diethyl 1,3-acetonedicarboxylate (120 g, 0.5934 mol) with stirring at $-18°$ C. After 24 hours at room temperature, the excess amine and water were removed under rotary evaporation and finally by azeotropic distillation with benzene to give a light yellow oil. It was kugelrohr distilled to give 52 g of light yellow oil as product (30%), $n_D^{25}$ 1.4887.

Anal. Calc'd. for $C_{12}H_{21}N_1O_4$: C, 59.24; H, 8.70; N, 5.76; Found: C, 59.32; H, 8.80; N, 5.80.

Step B: Preparation of diethyl 3-isopropylamino-2-(trifluoroacetyl)-2-pentenedioate:

To an ice-cooled solution of product of Step A (6 g, 0.025 mol) in tetrahydrofuran (200 ml) was added triethylamine (4.1 ml, 0.0296 mol) and to this solution was added slowly trifluoroacetic anhydride (6 ml, 8.9 g, 0.042 mol). After stirring at room temperature for 30 minutes, the solution was concentrated, quenched with water and dried over magnesium sulfate and concentrated to give a light yellow oil. The volatile material was removed by kugelrohr distillation to give 7 g of residual oil as product (82%), $n_D^{25}$ 1.4765.

Anal. Calc'd. for $C_{14}H_{20}F_3N_1O_5$: C, 49.56; H, 5.94; F, 16.80; N, 4.13; Found: C, 49.81; H, 5.62; F, 17.46; N, 4.37.

Step C: Preparation of pyridinedicarboxylate product:

To a solution of 6.74 g (0.02 mol) of product at Step B in 20 ml of THF was added 5.0 g (0.044% mol) of potassium t-butoxide. An exotherm raising the reaction temperature to 60° C. and a change in the solution to a deep red color were observed. To this solution 18 g (0.15 mol) of CF$_2$ClCN were added. The reaction mixture was then poured into 10% HCl, extracted with Et$_2$O, and the Et$_2$O layer was washed with H$_2$O and dried (MgSO$_4$). Solvent was removed in vacuo affording 9.87 g of a brownish-orange oil. Crude was kugelrohr distilled at 100°–110° C./67 Pa, followed by HPLC purification using 4% EtOAc/cyclohexane as eluting solvent to give 2.5 g of a yellow oil. This oil was kugelrohr distilled again at 110°–118° C./53 Pa affording 2.18 g (25%) of product as a light yellow oil, $n_D^{25}$ 1.4713.

Anal. Calc'd. for $C_{16}H_{18}F_5Cl_1N_2O_4$: C, 44.40; H, 4.19; N, 6.47; Cl, 8.19; Found: C, 44.43; H, 4.19; N, 6.42; Cl, 8.22%.

EXAMPLE 12

3,5-Dimethyl,4-(cyclopropylamino)-2,6-bis (pentafluoroethyl)-3,5-pyridinedicarboxylate,hydrate Step B: Preparation of dimethyl-3-(cyclopropylamino)-2-(pentafluoropropionyl)-2-pentenedioate To a solution of 10g (0.047 mol) of product from Step A of Example 4 in 100 ml of ether was added 18.6 g (0.06 mol) of pentafluoropropionic anhydride slowly. After 3 hours, the mixture was diluted with ether, washed with one 200 ml portion of 5% HCl, one 200 ml portion of 5% NaHCO$_3$ and one 200 ml portion of water. The pentenedioate compound was then dried (CaSO$_4$), filtered and concentrated to give 12 g (71%) of product as a yellow solid; mp 32°–34° C.

Anal. Calc'd. for $C_{13}H_{14}F_5O_5$: C, 43.46; H, 3.93; N, 3.90; Found: C, 43.77; H, 3.89; N, 3.72.

Step C: Preparation of pyridinedicarboxylate product:

To a solution of 4 g (0.011 mol) of product of Step A and 1.7 g (0.011 mol) of DBU in dimethoxyethane at 45° C. was bubbled pentafluoropropionitrile. After 1 hour heat was removed and the mixture was diluted with ether and washed with one 500 ml portion of 5% HCl, one 500 ml portion of 5% NaOH and one 500 ml portion of 5% HCl. The organic layer was dried (CaSO$_4$), filtered and concentrated to 4.6 g (87%) of red oil. Trituration with petroleum ether gave 4.5 g of product as a yellow solid; mp 49°–50° C.

Anal. Calc'd. for $C_{16}H_{12}F_{10}N_2O_4 \cdot 1/4H_2O$: C, 39.16; H, 2.57; N, 5.71; Found: C, 39.06; H, 2.43; N, 5.86.

Using the process of this invention, additional compounds shown in the following Table 1 were prepared.

TABLE I

| Example | R$_2$ | R | R$_3$ | R$_1$ | mp | $n_D^{25}$ |
|---|---|---|---|---|---|---|
| 13 | CF$_3$ | CH$_3$ | cyclopropyl | CF$_2$CF$_3$ | | 1.4541 |
| 14 | CF$_3$ | CH$_3$ | isopropyl | CF$_2$Cl | 34–36 | |
| 15 | CF$_3$ | CH$_3$ | cyclopropyl | CF$_2$Cl | 77–78 | |

Although the process has been described and exemplified with respect to specific conditions, the details thereof are not to be construed as limitations because many modifications and variations thereof are possible. The invention is therefore intended to be limited only by the following claims.

What is claimed is:

1. A process for the preparation of a compound of the formula

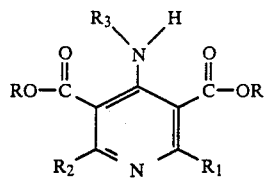

wherein $R_1$ and $R_2$ are independently selected from fluorinated and chlorofluorinated lower alkyl radicals; R is lower alkyl; $R_3$ is independently selected from lower alkyl, cycloalkyl, and aralkyl which comprises:

(a) reacting an acetonediester of the formula

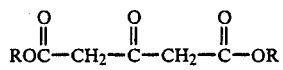

with a primary amine of the formula

to form an enamine;

(b) reacting the enamine with a carboxylic acid anhydride or halide of the formula

wherein X is

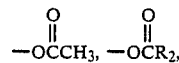

or a halogen and $R_2$ is the corresponding fluorinated or chlorofluorinated lower alkyl radical of the product compound to form a 2-alkylcarbonyl-3-amino-2-pentenedicarboxylate; and (c) reacting the pentenedicarboxylate with a halogenated alkylnitrile of the formula $R_1CN$ wherein $R_1$ is the corresponding fluorinated or chlorofluorinated radical of the product compound in the presence of a base to form the 4-amino-3,5 pyridinedicarboxylate product.

2. The process of claim 1 wherein $R_1$ and $R_2$ are independently selected from fluorinated and chlorofluorinated methyl and ethyl radicals.

3. The process of claim 1 wherein the step (a) process is conducted at a temperature in the range of 0° to 50° C.

4. The process of claim 2 wherein a solvent selected from ethers and tetrahydrofuran is employed in step (b).

5. The process of claim 2 wherein step (b) reaction is conducted at a temperature below the boiling point of the solvent.

6. The process of claim 2 wherein a solvent selected from ethers dimethoxyethane and toluene is employed in step (c).

7. The process of claim 5 wherein an amine base is present in step (c).

8. The process of claim 1 wherein $R_1$ and $R_2$ are both trifluoromethyl radicals.

* * * * *